(12) United States Patent
Ohji et al.

(10) Patent No.: US 8,265,371 B2
(45) Date of Patent: Sep. 11, 2012

(54) METHOD FOR EVALUATING CELL DETACHMENT, METHOD OF DETACHING CULTURED CELL, APPARATUS FOR EVALUATING CELL DETACHMENT AND AUTOMATED CELL CULTURE APPARATUS

(75) Inventors: Osamu Ohji, Hyogo (JP); Toshihisa Doi, Moscow (RU)

(73) Assignee: Kawasaki Jukogyo Kabushiki Kaisha, Kobe-shi (JP)

( * ) Notice: Subject to any disclaimer, the term of this patent is extended or adjusted under 35 U.S.C. 154(b) by 763 days.

(21) Appl. No.: 12/296,528

(22) PCT Filed: Apr. 12, 2007

(86) PCT No.: PCT/JP2007/058031
§ 371 (c)(1),
(2), (4) Date: Jun. 10, 2009

(87) PCT Pub. No.: WO2007/119764
PCT Pub. Date: Oct. 25, 2007

(65) Prior Publication Data
US 2009/0304257 A1    Dec. 10, 2009

(30) Foreign Application Priority Data
Apr. 12, 2006    (JP) .................................. 2006-109545

(51) Int. Cl.
*G06K 9/00* (2006.01)
(52) U.S. Cl. .................................... 382/133; 435/287.1
(58) Field of Classification Search .......... 382/128–134; 356/39–42, 344; 377/10–12; 702/19–21
See application file for complete search history.

(56) References Cited

U.S. PATENT DOCUMENTS

| | | | | |
|---|---|---|---|---|
| 2008/0075350 A1* | 3/2008 | Nitta | ............................. | 382/133 |
| 2008/0201083 A1* | 8/2008 | Hata et al. | ....................... | 702/21 |
| 2008/0279441 A1* | 11/2008 | Matsuo et al. | ................ | 382/133 |
| 2009/0081769 A1* | 3/2009 | Kiyota et al. | .............. | 435/288.7 |
| 2009/0087075 A1* | 4/2009 | Kii et al. | ....................... | 382/133 |

FOREIGN PATENT DOCUMENTS

| | | |
|---|---|---|
| JP | 2002-218967 | 8/2002 |
| JP | 2003-235540 | 8/2003 |
| JP | 2005-027623 | 2/2005 |
| JP | 2006-149268 | 6/2006 |
| JP | 2006-271210 | 10/2006 |
| WO | WO-2005/059088 | 6/2005 |

OTHER PUBLICATIONS

International Search Report for PCT/JP2007/058031, dated Jun. 14, 2007.
Umegaki et al., "Assessment of cell detachment and growth potential of human keratinocyte based on observed changes in individual cell area during trypsinization", *Biochemical Engineering Journal*, vol. 17, No. 1, pp. 49-55, Jan. 2004.
Supplementary European Search Report for EP 07 74 1467, mailed Apr. 16, 2009.

* cited by examiner

*Primary Examiner* — Gerald J. O'Connor
*Assistant Examiner* — Jonathan K Ng
(74) *Attorney, Agent, or Firm* — Marshall, Gerstein & Borun, LLP

(57) ABSTRACT

A novel method for evaluating cell detachment which can be used in passage operation and the like in culture of adhesive cells; a method of detaching a cultured cell utilizing the same; an apparatus for evaluating cell detachment for carrying out the aforementioned method for evaluating cell detachment; and an automated cell culture apparatus in which the apparatus is used are provided.

14 Claims, 4 Drawing Sheets

METHOD FOR EVALUATING CELL DETACHMENT, METHOD OF DETACHING CULTURED CELL, APPARATUS FOR EVALUATING CELL DETACHMENT AND AUTOMATED CELL CULTURE APPARATUS

TECHNICAL FIELD

The present invention relates to a method for evaluating cell detachment, a method of detaching a cultured cell, an apparatus for evaluating cell detachment and an automated cell culture apparatus. More particularly, the invention relates to: a method for evaluating cell detachment in order to determine, in detachment of a cultured cell from the culture vessel after cell cultivation, as to whether the cultured cell was satisfactorily detached from the culture vessel or not; a method of detaching a cultured cell utilizing the same; an apparatus for evaluating cell detachment for carrying out the aforementioned method for evaluating cell detachment; and an automated cell culture apparatus in which the apparatus is used.

BACKGROUND ART

In recent years, regenerative medicine in which a cell or a tissue of skin, cartilage, bone, blood vessel, organ or the like in human body is removed and cultured, and thereafter used in a treatment of the same person or other person has been developed. The practical application of this technique has been initiated in part. In such regenerative medicine, a small amount of cells collected from a human body are cultured ex vivo, and the cell culture is conducted using a culture vessel such as a petri dish via several times of passage operations. In the passage operation of adhesive cells, the cultured cells attached to the bottom face of the culture vessel are detached using a detachment solution containing, for example, trypsin or the like, and a part thereof is transferred to another culture vessel including a fresh medium. In such procedure, since trypsin used in detachment of the cultured cells leads to degradation of proteins, it is necessary to stop the degradation of proteins by adding a detachment stop solution after executing the detachment of the cultured cells for a short period of time.

However, since detachment of the cultured cells from a culture vessel requires visual observation using a microscope, variation among individual operators is likely to occur. Additionally, also in cases in which automation of the culture apparatus is intended, there still involves a problem that human intervention cannot be avoided in the step of evaluating the detachment of the cultured cell.

In order to solve this problem, a method has been investigated in which an attached cell and a detached cell are discriminated on the basis of the size of the cell area on an image in view of the phenomenon that the cultured cell attached to the culture vessel is found to cover a larger area viewed on the image, while the detached cell is found to cover a smaller area viewed on the image since it takes an approximately spherical shape due to surface tension. However, it is necessary to identify the area before the detachment and the area during/following a detachment treatment for each cell in this method, and thus this method is accompanied by many problems in practical use for cell culture, although it can be used for just research purposes.

Patent Document 1: Japanese Unexamined Patent Application, First Publication No. Hei 2003-235540

DISCLOSURE OF THE INVENTION

Problems to be Solved by the Invention

The present invention was made in order to solve the problems in the aforementioned prior arts, and an object of the present invention is to provide: a novel method for evaluating cell detachment which can be used in passage operation and the like for culture of an adhesive cell; a method of detaching a cultured cell using the evaluation method; an apparatus for evaluating cell detachment for carrying out the aforementioned method for evaluating cell detachment; and an automated cell culture apparatus in which the apparatus is used.

Means for Solving the Problems

In the method for evaluating cell detachment of the present invention, cell detachment from a culture vessel is evaluated, and the method for evaluating cell detachment is characterized by including the steps of: taking a first image by imaging a certain position in a culture vessel; taking a second image by imaging the certain position after taking the first image and also after allowing the culture liquid in the culture vessel to flow; and evaluating the cell detachment from the culture vessel based on the position of the cell specified from the first image, and the position of the cell specified from the second image.

In addition, in the method for evaluating cell detachment of the present invention, cell detachment from a culture vessel is evaluated, and the method for evaluating cell detachment is characterized by including the steps of: taking a first image by imaging a certain position in a culture vessel; taking a second image by imaging the certain position after taking the first image and also after allowing the culture liquid in the culture vessel to flow; and evaluating the cell detachment from the culture vessel based on a cell area ratio A, a cell area ratio B, and a common area ratio C following determination of the common area ratio C for a section where the cell is present in both the first image and the second image based on the cell area ratio A for a section where the cell is present in the first image, and the cell area ratio B for a section where the cell is present in the second image.

The method of detaching cultured cells of the present invention is characterized by including the steps of: placing a detachment solution into a culture vessel for allowing the cultured cell to be detached from the culture vessel; evaluating the cell detachment from the culture vessel by the aforementioned method for evaluating cell detachment; and placing a detachment stop solution into the culture vessel.

The apparatus for evaluating cell detachment of the present invention for use in carrying out the aforementioned method for evaluating cell detachment is characterized by including a vibration exciter which allows the culture liquid in the culture vessel to turn into its flowing state; a device for taking an image for obtaining the first image and the second image; and a cell detachment evaluation means for evaluating the cell detachment from the culture vessel based on the position of the cell specified from the first image and on the position of the cell specified from the second image.

Furthermore, the apparatus for evaluating cell detachment of the present invention for use in carrying out the aforementioned method for evaluating cell detachment is characterized by including a vibration exciter which allows the culture liquid in the culture vessel to turn into its flowing state; a device for taking an image for obtaining the first image and the second image; and a cell detachment evaluation means for evaluating the cell detachment from the culture vessel based on the cell area ratio A, the cell area ratio B and the common area ratio C, in which the common area ratio C is determined based on the cell area ratio A and the cell area ratio B.

Moreover, the automated cell culture apparatus of the present invention is characterized by including the apparatus for evaluating cell detachment, and an operation robot for carrying the culture vessel.

Effects of the Invention

According to the method for evaluating cell detachment and the method of detaching cultured cells of the present invention, evaluation of detachment of a cultured cell without human intervention is enabled, and construction of an apparatus for evaluating cell detachment and an automated cell culture apparatus is enabled. In addition, variation of the evaluation results of the cell detachment depending on the subjectivity of individual operators is obviated, thereby enabling stable evaluation at a certain level. Accordingly, an apparatus for evaluating cell detachment and automated cell culture apparatus is provided which enables to obtain constantly specified cultured cells.

BRIEF DESCRIPTION OF THE DRAWINGS

FIGS. 1 (a) and 1 (b) show a view schematically illustrating a first image and a second image obtained by imaging at different time points under conditions in which the culture liquid flows, and FIG. 1 (c) shows a view schematically displaying the overlapped first image and second image.

DESCRIPTION OF REFERENCE NUMERALS AND SIGNS 1, 2 attached cell
3, 3' floating cell
4 intersection
10 equipment installation unit
11 operation robot
11a robot control apparatus
12 incubator
13 storage unit
14 operation unit
15 image-grabber unit
16 image processing apparatus
17 overall control apparatus
5 table
5a opening
6 culture vessel
7 lighting
8 microscope with camera
9 vibration exciter
9a vibration stage

BEST MODE FOR CARRYING OUT THE INVENTION

Figure 1:
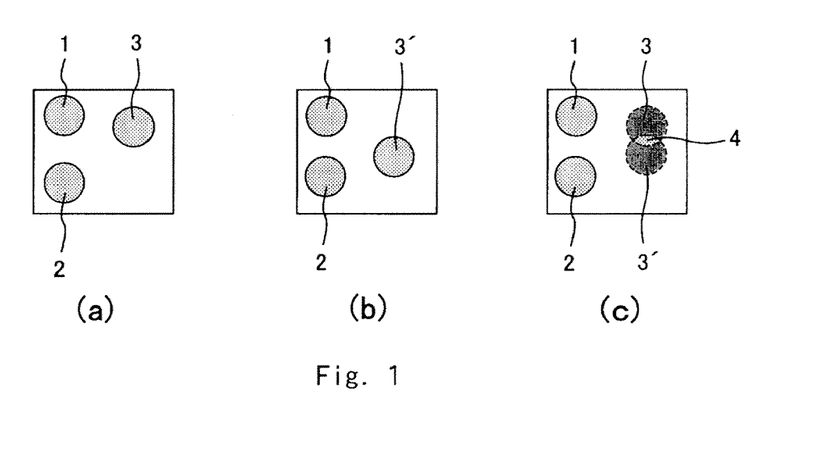

The method for evaluating cell detachment of the present invention is based on the fact that the position of a detached floating cell is changed when the culture liquid flows, although the position of the attached (undetached) cell is not changed even though the culture liquid flows due to vibration of the culture vessel since such cell is attached to, for example, the bottom face of a culture vessel such as a petri dish. FIG. 1 schematically illustrates a first image and a second image obtained by imaging at different time points in a flowable culture liquid. First, in a static state or a flowing state of the culture liquid, the first image shown in FIG. 1 (a) is taken, and subsequently, the second image shown in FIG. 1 (b) is taken after a lapse of a predetermined time (for example, after 0.1 sec to 1 sec) in a state in which the culture liquid flows. Comparison of the first image and the second image can lead to an evaluation that the cell 1 and cell 2 are attached cells which are attached to the culture vessel since the positions of the cell 1 and the cell 2 are unchanged. To the contrary, the position of cell 3 in the first image is migrated to the position of cell 3' in the second image, thereby capable of evaluating as a detached cell which was detached from the culture vessel. Therefore, when there are a large number of cells found at different positions between the first image and the second image, an evaluation can be made that the cell detachment has proceeded.

With respect to the position of the cell in the first image and the second image, the position of the center of gravity is determined for each cell, and an evaluation can be made it is an attached cell when the positions of the center of gravity are the same between the first image and the second image, while it is a floating cell when the positions of the center of gravity are different. Additionally, when the proportion of the floating cell accounting for the entire cells exceeds a predetermined proportion, an evaluation can be made that the cell detachment is completed.

Moreover, according to the method for evaluating cell detachment of the present invention, cell detachment can be also evaluated by means of the cell area ratio in the first image and the second image taken as described above. Hereinafter, a specific method for evaluating cell detachment based on the cell area ratio is explained.

Figure 2:
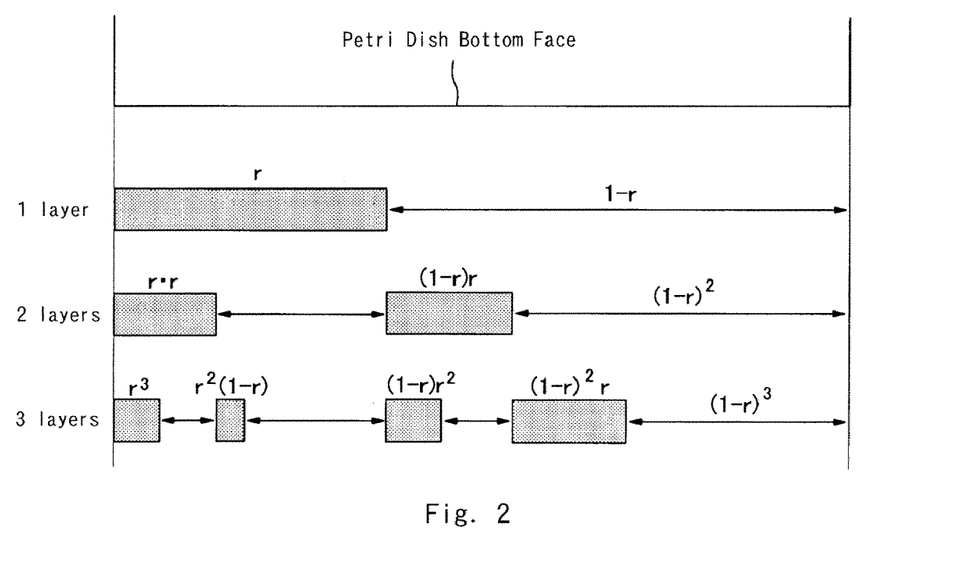
FIG. 2 shows a view illustrating the method for evaluating cell detachment in terms of probability when the overlap of the detached cell is considered.

When the presence or absence of the detached cell is evaluated in terms of probability based on the image of the culture vessel, possibility of overlap of the detached cell with the attached cell and other floating cell must be considered. FIG. 2 illustrates the method for evaluating cell detachment in terms of probability when the overlap of the detached cells is considered. The "area ratio" referred to herein means the value derived by dividing the area of, for example, a section where the cell is either present or absent on the culture vessel such as a petri dish or the like by the area of the bottom of the culture vessel. Furthermore, when considered on an image taken for a part of the culture vessel, this area ratio may be supposed to be a value derived by dividing the area of a section where the cell is present or a section where the cell is absent in the image by the area of the entire face of the obtained image.

When considered on a culture vessel such as a petri dish or the like, "total area" of the floating cell refers to sum total of the area occupied by the floating cells on the bottom face of the culture vessel, and in the case in which the floating cells multiply overlap, it should be a value derived by multiple estimation of the areas. In addition, "total area ratio" of the floating cell is a value derived by dividing the total area of the floating cell by the area of the bottom of the culture vessel.

Moreover, when considered on an image taken in part of the culture vessel, "total area" of the floating cell refers to sum total of the area occupied by the floating cells on the obtained image, and in the case in which the floating cells multiply overlap, it should be a value derived by multiple integration of the areas. In addition, "total area ratio" of the floating cell is a value derived by dividing the total area of the floating cell by the entire area of the obtained image.

Furthermore, when considered on the culture vessel such as a petri dish or the like, "projected area" of the floating cell refers to the area determined when the region where the floating cells are present is projected on the bottom face of the culture vessel, and also in the case in which the floating cells multiply overlap, it should be a value derived by estimation assuming as one cell. In addition, "projected area ratio" of the floating cell is a value derived by dividing the projected area of the floating cell by the area of the bottom face of the culture vessel.

Also, when considered on an image taken in part of the culture vessel, "projected area" of the floating cell refers to the area determined when the region where the floating cells are present is projected on the image face, and also in the case in which the floating cells multiply overlap, it should be a value derived by estimation assuming as one cell. In addition, "projected area ratio" of the floating cell is a value derived by dividing the projected area of the floating cell by the entire area of the obtained image.

As shown in FIG. 2, the entire area ratio of the bottom face of the petri dish is 1 according to the aforementioned definition. Provided that probability of the presence of the floating cell in a layer among overlapping n layers is defined as r: sum total of the area ratio of the section where any cell is not present through to the layer; sum total of the projected area ratio of the cells through to the layer; and total area ratio of the cells through to the layer may be determined for each layer as presented in Table 1.

TABLE 1

| Number of layer(s) | Area ratio of the section where any cell is not present through to the layer | Projected area ratio of the cells through to the layer | Total area ratio of the cells through to the layer |
|---|---|---|---|
| 1 | $1 - r$ | $1 - (1 - r)$ | $r$ |
| 2 | $(1 - r)^2$ | $1 - (1 - r)^2$ | $2r$ |
| 3 | $(1 - r)^3$ | $1 - (1 - r)^3$ | $3r$ |
| n | $(1 - r)^n$ | $1 - (1 - r)^n = \sum_{j=1}^{n} (-1)^{j-1} {}_nC_j r^j$ | $nr$ |

First, a case in which there is no overlap of the floating cell is assumed in FIG. 2. This corresponds to the case in which the number of the layer is 1 in FIG. 2 and Table 1. Provided that the total area ratio of the floating cell is defined as s, and the projected area ratio of the floating cell is defined as t, $$t = s \qquad (1)$$

under such condition.

Next, a case in which the floating cells may overlap up to two layers is assumed. This corresponds to the case in which the number of the layers is 2 in FIG. 2 and Table 1. Under such condition, $$t = s - s^2/4 \qquad (2).$$

Therefore, for example, t is 0.750 when s is 1; t is 0.438 when s is 0.5; and t is 0.278 when s is 0.3 as derived according to the formula (2).

Further, a case in which the floating cells may overlap up to n layers is assumed. This corresponds to the case in which the number of the layers is n in FIG. 2 and Table 1. Under such condition, t is represented by the following formula (3) below:

$$\begin{aligned}
t &= \lim_{n \to \infty} \sum_{j=1}^{n} (-1)^{j-1} {}_nC_j r^j \\
&= \lim_{n \to \infty} \left( \frac{n}{1!}r - \frac{n(n-1)}{2!}r^2 + \frac{n(n-1)(n-2)}{3!}r^3 - \frac{n(n-1)(n-2)(n-3)}{4!}r^4 + \dots \right) \\
&= \lim_{n \to \infty} \left( \frac{ns}{1!n} - \frac{n(n-1)s^2}{2!n^2} + \frac{n(n-1)(n-2)s^3}{3!n^3} - \frac{n(n-1)(n-2)(n-3)s^4}{4!n^4} + \dots \right) \\
&= s - s^2/2! + s^3/3! - s^4/4! + s^5/5! - \dots \\
&= (s^1/1! + s^3/3! + s^5/5! + \dots) - (s^0/0! + s^2/2! + s^4/4! + \dots) + 1 \\
&= \sinh s - \cosh s + 1 \\
&= (e^s - e^{-s})/2 - (e^s + e^{-s})/2 + 1 \\
&= 1 - e^{-s}
\end{aligned}$$

Therefore, for example, t is 0.638 when s is 1: t is 0.393 when s is 0.5; and t is 0.259 when s is 0.3 as derived according to the formula (3).

Specific Method for Evaluating Cell Detachment

On the basis of the foregoing description, a method for evaluating cell detachment based on the area ratio of the cells is specifically explained on each case with regard to the first image taken in a static state or flowing state of the culture liquid, or to the second image taken after a lapse of a predetermined time in the flowing state of the culture liquid. Mathematical formulae for explaining the following each case is summarized in Table 2.

Condition 1: Case in which any Attached Cell does not Overlap With any Floating Cell, and any Floating Cells do not Overlap First, a case in which any cell attached to the culture vessel, and any floating cell detached from the culture vessel do not overlap one another is explained. This condition can be applied to the case in which the specific gravity of the cell is sufficiently greater than the specific gravity of the liquid in a culture vessel. In this case, the position of the floating cell is changed by the vibration, but the cells do not overlap.

Based on the cell area ratio A of the section where the cell is present in the first image, and the cell area ratio B of the section where the cell is present in the second image, the common area ratio C is determined for a section where the cell is present in both the first image and the second image as shown in FIG. 1 (c). Provided that the following definitions: f as area ratio of the attached cell; $s_1$ as total area ratio of the floating cell in the first image; $t_1$ as projected area ratio of the floating cell in the first image; $x_1$ as cell detachment rate in the first image; $s_2$ as total area ratio of the floating cell in the second image; $t_2$ as projected area ratio of the floating cell in the second image; and $x_2$ as cell detachment rate in the second image are made, the cell area ratios A and B are represented by the following formulae:

$$A=f+t_1$$

$$B=f+t_2,$$

since they are sum totals of the area ratio of the attached cell f, and the projected area ratio of the floating cell $t_1$ and $t_2$, respectively. In addition, since the common area ratio C is a sum total of the area ratio of the attached cell f and the intersection 4 of the floating cell in FIG. 1 (*c*), C is represented by the following formula:

$$C=f+t_1 \cdot t_2/(1-f).$$

Therefore, f is represented by the following formula:

$$f=(C-A \cdot B)/(1+C-A-B).$$

Since the floating cells do not overlap one another, $s_1=t_1$, and $s_2=t_2$. Accordingly, $s_1$ and $s_2$ are represented by the following formulae:

$$s_1=A-f=A-(C-A \cdot B)/(1+C-A-B), \text{ and}$$

$$s_2=B-f=A-(C-A \cdot B)/(1+C-A-B),$$

and the detachment rate is determined by the following formulae:

$$x_1=s_1/(f+s_1)=s_1/A, \text{ and}$$

$$x_2=s_2/(f+s_2)=s_2/B$$

wherein, determination on $x_1$ and $x_2$ would not differ significantly, since their only one difference is that $x_1$ is determined on the first image, while $x_2$ is determined on the second image.

Thus determined $x_1$ or $x_2$ is compared with a predetermined threshold, and the evaluation that the detachment of the cultured cell was completed can be made when the detachment rate that is greater than the threshold is achieved. Such a threshold is preferably specified empirically by carrying out a preliminary experiment.

Condition 2: Case in which an Attached Cell May Overlap with a Floating Cell, but any Floating Cells do not Overlap Next, a case in which a cell attached to the culture vessel may overlap with a floating cell detached from the culture vessel, but the floating cells do not overlap one another is explained. This condition can be applied to the case in which the specific gravity of the cell is greater to some extent than the specific gravity of liquid in a culture vessel, or the case in which the specific gravity of the cell is smaller to some extent than the specific gravity of the liquid in the culture vessel. In these cases, vibration may result in migration of the floating cell on or above the attached cell, but the floating cells do not overlap one another due to a great specific gravity of the cell.

Using the cell area ratio A, the cell area ratio B, the common area ratio C, the area ratio of the attached cell f, the total area ratio $s_1$, the projected area ratio $t_1$, the cell detachment rate $x_1$, the total area ratio $s_2$, the projected area ratio $t_2$, and the cell detachment rate $x_2$, the cell area ratios A and B are represented by the following formulae:

$$A=f+t_1-f \cdot t_1$$

$$B=f+t_2-f \cdot t_2,$$

since they are to be derived by subtracting the overlapping section of the attached cell and floating cell from the sum totals of the area ratio of the attached cell f, and the projected area ratio of the floating cell $t_1$ and $t_2$, respectively.

In addition, since the common area ratio C is a sum total of the area ratio of the attached cell f and the intersection 4 of the floating cell in FIG. 1 (*c*), C is represented by the following formula:

$$C=f+(1-f) \cdot t_1 \cdot t_2.$$

Furthermore, the formulae:

$$t_1=(A-f)/(1-f), \text{ and}$$

$$t_2=(B-f)/(1-f)$$

would lead to the formula:

$$f=(C-A \cdot B)/(1+C-A-B).$$

Since the floating cells do not overlap one another, $s_1=t_1$, and $s_2=t_2$. Accordingly, the detachment rate is determined by the following formulae:

$$x_1=s_1/(f+s_1), \text{ and}$$

$$x_2=s_2/(f+s_2)$$

wherein, determination on $x_1$ and $x_2$ would not differ significantly as described above.

Thus determined $x_1$ or $x_2$ is compared with a predetermined threshold, and the evaluation that the detachment of the cultured cell was completed can be made when the detachment rate that is greater than the threshold is achieved. Such a threshold is preferably determined empirically by carrying out a preliminary experiment.

Condition 3: Case in which an Attached Cell May Overlap with a Floating Cell, and Floating Cells May Also Overlap in Duplicate at Most Next, a case in which a cell attached to the culture vessel may overlap with a floating cell detached from the culture vessel, and the floating cells may also overlap one another in duplicate at most is explained. This condition can be applied to the case in which the specific gravity of the cell is a little greater than the specific gravity of the liquid in a culture vessel, or the case in which the specific gravity of the cell is a little smaller than the specific gravity of the liquid in the culture vessel. In these cases, since the specific gravity of the liquid in the culture vessel is approximate to the specific gravity of the cell, the floating cells may be somewhat stirred by vibration in the liquid in the culture vessel.

Using the cell area ratio A, the cell area ratio B, the common area ratio C, the area ratio of the attached cell f, the total area ratio $s_1$, the projected area ratio $t_1$, the cell detachment rate $x_1$, the total area ratio $s_2$, the projected area ratio $t_2$, and the cell detachment rate $x_2$, the cell area ratios A and B are represented by the following formulae:

$$A=f+t_1 f \cdot t_1$$

$$B=f+t_2-f \cdot t_2,$$

since they are to be derived by subtracting the overlapping section of the attached cell and floating cells from the sum totals of the area ratio of the attached cell f, and the projected area ratio of the floating cell $t_1$ and $t_2$, respectively.

In addition, since the common area ratio C is a sum total of the area ratio of the attached cell f and the intersection 4 of the floating cells in FIG. 1 (*c*), C is represented by the following formula:

$$C=f+(1-f) \cdot t_1 \cdot t_2.$$

Furthermore, the formulae:

$$t_1=(A-f)/(1-f), \text{ and}$$

$$t_2=(B-f)/(1-f)$$

would lead to the formula:

$$f=(C-A\cdot B)/(1+C-A-B).$$

Also, according to the above formula (2), $$t_1=s_1-s_1^2/4, \text{ and}$$

$$t_2=s_2-s_2^2/4.$$

Thus, $s_1$ and $s_2$ are represented by the following formulae:

$$s_1=2-2(1-t_1)^{1/2}, \text{ and}$$

$$s_2=2-2(1-t_2)^{1/2},$$

whereby the detachment rate is determined by the following formulae:

$$x_1=s_1/(f+s_1), \text{ and}$$

$$x_2=s_2/(f+s_2)$$

wherein, determination on $x_1$ and $x_2$ would not differ significantly as described above.

Thus determined $x_1$ or $x_2$ is compared with a predetermined threshold, and the evaluation that the detachment of the cultured cell was completed can be made when the detachment rate that is greater than the threshold is achieved. Such a threshold is preferably specified empirically by carrying out a preliminary experiment.

Condition 4: Case in which an Attached Cell May Overlap with a Floating Cell, and Floating Cells May Also Overlap Multiply Next, a case in which a cell attached to the culture vessel may overlap with a floating cell detached from the culture vessel, and the floating cells may also overlap multiply one another is explained. This condition can be applied to the case in which the specific gravity of the liquid in a culture vessel is almost equal to the specific gravity of the cell. In this case, since the specific gravity of the liquid in the culture vessel is almost equal to the specific gravity of the cell, the floating cells migrate randomly due to vibration in the liquid in the culture vessel.

Using the cell area ratio A, the cell area ratio B, the common area ratio C, the area ratio of the attached cell f, the total area ratio $s_1$, the projected area ratio $t_1$, the cell detachment rate $x_1$, the total area ratio $s_2$, the projected area ratio $t_2$, and the cell detachment rate $x_2$, the cell area ratios A and B are represented by the following formulae:

$$A=f+t_1-f\cdot t_1$$

$$B=f+t_2-f\cdot t_2,$$

since they are to be derived by subtracting the overlapping section of the attached cell and floating cell from the sum totals of the area ratio of the attached cell f, and the projected area ratio of the floating cell $t_1$ and $t_2$, respectively.

In addition, since the common area ratio C is a sum total of the area ratio of the attached cell f and the intersection 4 of the floating cells in FIG. 1 (c), C is represented by the following formula:

$$C=f+(1-f)\cdot t_1\cdot t_2.$$

Furthermore, the formulae:

$$t_1=(A-f)/(1-f), \text{ and}$$

$$t_2=(B-f)/(1-f)$$

would lead to the formula:

$$f=(C-A\cdot B)/(1+C-A-B).$$

Also, according to the above formula (3), $$t_1=1-\exp(-s_1), \text{ and}$$

$$t_2=1-\exp(-s_2).$$

Thus, $s_1$ and $s_2$ are represented by the following formulae:

$$s_1=-\ln(1-t_1), \text{ and}$$

$$s_2=-\ln(1-t_2),$$

whereby the detachment rate is determined by the following formulae:

$$x_1=s_1/(f+s_1), \text{ and}$$

$$x_2=s_2/(f+s_2)$$

wherein, determination on $x_1$ and $x_2$ would not differ significantly as described above.

Thus determined $x_1$ or $x_2$ is compared with a predetermined threshold, and the evaluation that the detachment of the cultured cell was completed can be made when the detachment rate that is greater than the threshold is achieved. Such a threshold is preferably specified empirically by carrying out a preliminary experiment.

TABLE 2

|  | Condition 1 | Condition 2 | Condition 3 | Condition 4 |
|---|---|---|---|---|
| Basic formula | $A = f + t_1$<br>$B = f + t_2$<br>$C = f + t_1 \cdot t_2/(1-f)$ | $A = f + t_1 - f \cdot t_1$<br>$B = f + t_2 - f \cdot t_2$<br>$C = f + (1-f)t_1 \cdot t_2$ | same as on the left | same as on the left |
| Relationship between projected area ratio of floating cell and area ratio of adhered cell | $t_1 = A - f$<br>$t_2 = B - f$ | $t_1 = (A-f)/(1-f)$<br>$t_2 = (B-f)/(1-f)$ | same as on the left | same as on the left |
| Formula for calculating area ratio of attached cell | $f = (C - AB)/(1 + C - A - B)$ | same as on the left | same as on the left | same as on the left |
| Relationship between total area ratio of floating cell and projected area ratio of floating cell | $t_1 = s_1$<br>$t_2 = s_2$<br>$s_1 = t_1$<br>$s_2 = t_2$ | same as on the left | $t_1 = s_1 - s_1^2/4$<br>$t_2 = s_2 - s_2^2/4$<br>$s_1 = 2 - 2(1-t_1)^{1/2}$<br>$s_2 = 2 - 2(1-t_2)^{1/2}$ | $t_1 = 1 - \exp(-s_1)$<br>$t_2 = 1 - \exp(-s_2)$<br>$s_1 = -\ln(1 - t_1)$<br>$s_2 = -\ln(1 - t_2)$ |
| Detachment rate | $x_1 = s_1/(f + s_1) = s_1/A$<br>$x_2 = s_2/(f + s_2) = s_2/B$ | $x_1 = s_1/(f + s_1)$<br>$x_2 = s_2/(f + s_2)$ | same as on the left | same as on the left |
| Remarks (Condition) | no cell overlapping | No floating cell overlapping, but adhesion cell overlapping with floating cell | floating cells overlapping one another in duplicate at most | Multiply overlapping |

Simulation

In the four conditions described above, the cell area ratio A, the cell area ratio B and the common area ratio C were specified, and the cell detachment rate in the first image $x_1$, was determined. The results are shown in Table 3.

TABLE 3

| Image 1 area ratio A | Image 2 area ratio B | Common area ratio C | Detachment rate determined on the first image: $x_1$ | | | |
|---|---|---|---|---|---|---|
| | | | Condition 1 | Condition 2 | Condition 3 | Condition 4 |
| 0.70 | 0.70 | 0.60 | 0.214 | 0.377 | 0.400 | 0.424 |
| | | 0.50 | 0.857 | 0.870 | 0.894 | 0.916 |
| 0.60 | 0.60 | 0.50 | 0.222 | 0.349 | 0.365 | 0.381 |
| | | 0.40 | 0.667 | 0.714 | 0.745 | 0.776 |
| 0.50 | 0.50 | 0.40 | 0.250 | 0.348 | 0.360 | 0.373 |
| | | 0.30 | 0.667 | 0.706 | 0.730 | 0.754 |
| 0.40 | 0.40 | 0.30 | 0.300 | 0.373 | 0.384 | 0.394 |
| | | 0.20 | 0.750 | 0.769 | 0.786 | 0.802 |
| 0.30 | 0.30 | 0.30 | 0.000 | 0.000 | 0.000 | 0.000 |
| | | 0.25 | 0.179 | 0.225 | 0.228 | 0.231 |
| | | 0.20 | 0.389 | 0.438 | 0.447 | 0.457 |
| | | 0.15 | 0.637 | 0.663 | 0.676 | 0.689 |
| | | 0.10 | 0.933 | 0.935 | 0.939 | 0.944 |
| | | 0.09 | 1.000 | 1.000 | 1.000 | 1.000 |
| 0.30 | 0.32 | 0.15 | 0.660 | 0.684 | 0.697 | 0.710 |
| | 0.30 | | 0.637 | 0.663 | 0.676 | 0.689 |
| | 0.28 | | 0.614 | 0.643 | 0.656 | 0.669 |
| | | | No cell overlapping | No floating cell overlapping, but attached cell overlapping with floating cell | floating cells overlapping one another in duplicate at most | Multiplly |

Upon taking the image in effect, focusing may be difficult because the cells are often transparent, and a true value for the area of each cell may not be calculated due to the image processing algorithm employed. However, when the area of each cell is determined to derive a larger or smaller value than the true value at a certain rate, the method of the present invention may be advantageous in that the influences can be canceled in the process of the calculation, whereby final influences on the calculation result may be avoided.

Figure 3:
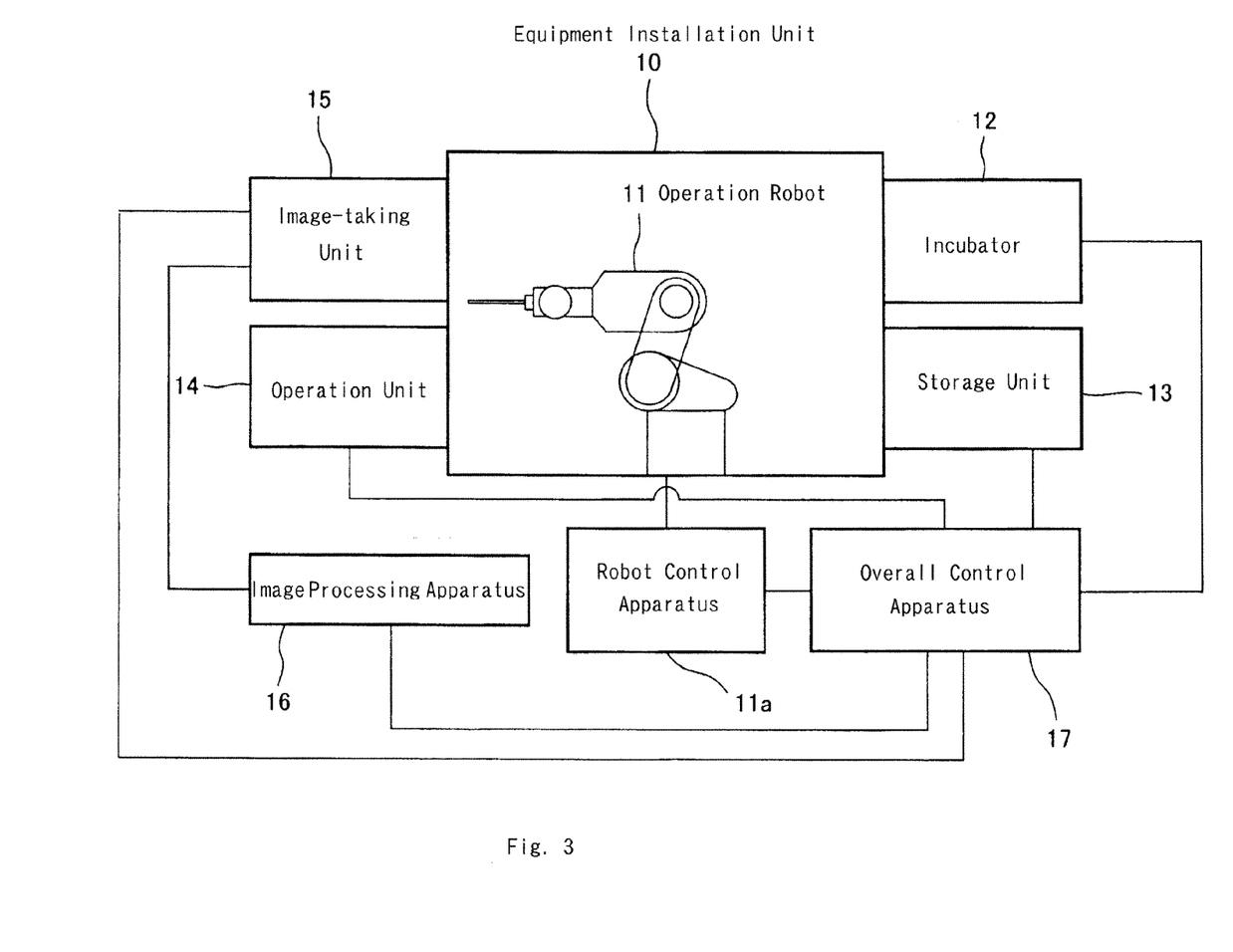
FIG. 3 shows a view schematically illustrating construction of the automated cell culture apparatus according to one embodiment for carrying out the method for evaluating cell detachment of the present invention.

FIG. 3 shows a schematic construction of the automated cell culture apparatus according to one embodiment of the present invention for carrying out the foregoing method for evaluating cell detachment. The automated cell culture apparatus of this embodiment includes an equipment installation unit 10 in the center, and the equipment installation unit 10 is equipped with an operation robot 11 that operates under the control of a robot control apparatus 11a. In addition, an incubator 12 for performing cell culture in a culture vessel such as a petri dish placed therein, a storage unit 13 for storing tools and reagents required for the cell culture, a operation unit 14 for carrying out operation such as addition of a detachment solution to the culture vessel or centrifugal separation, and a image-grabber unit 15 used for obtaining the image in the culture vessel are provided adjacent to the equipment installation unit 10. A shutter (not shown in the Figure) is provided between the equipment installation unit 10 and each of the operation robot 11, the incubator 12, the storage unit 13, the operation unit 14 and the image-grabber unit 15, and this shutter is constructed such that it can be opened only when operation by the operation robot 11 is necessary. The system is constructed such that the image obtained at the image-grabber unit 15 is transferred to and processed at the image processing apparatus 16. In this embodiment, the robot control apparatus 11a, the incubator 12, the storage unit 13, the operation unit 14, the image-grabber unit 15 and the image processing apparatus 16 are operated under the control of overall control apparatus 17 which can serve as a cell detachment evaluation means.

Figure 4:
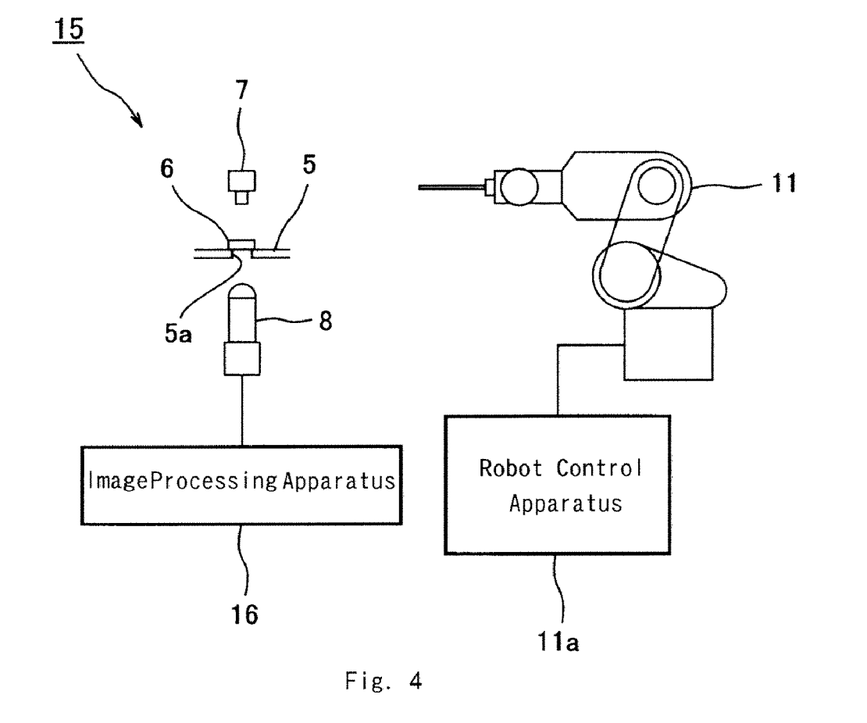
FIG. 4 shows a view illustrating details of the units for taking image according to one embodiment of the present invention.

FIG. 4 shows details of the image-grabber unit 15, and also schematically shows the image processing apparatus 16, the operation robot 11 and the robot control apparatus 11a in conjunction for explanatory purpose. As shown in the Figure, the image-grabber unit 15 includes a table 5 having an opening 5a, an lighting 7 for lighting the culture vessel 6 on the table 5, and a microscope with camera 8.

Figure 6:
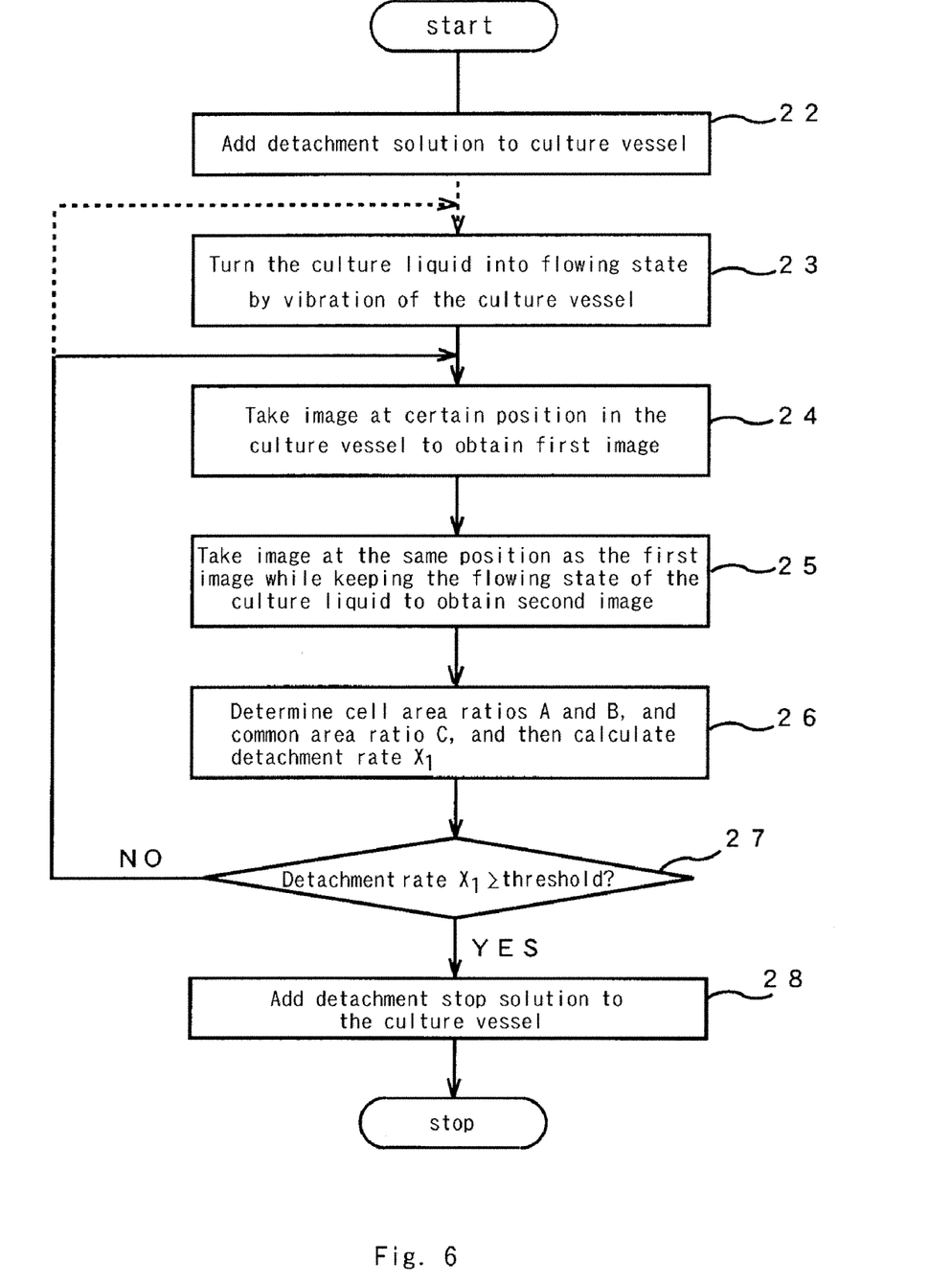
FIG. 6 shows a flow chart illustrating the method of detaching a cell according to one embodiment of the present invention.

The automated cell culture apparatus of this embodiment operates, for example, according to the flow chart shown in FIG. 6 illustrating the method of detaching a cell, as follows. First, the shutter between the equipment installation unit 10 and the incubator 12 is opened. Next, the operation robot 11 holds and removes the culture vessel in the incubator 12, which is transferred to the operation unit 14. In the operation unit 14, a detachment solution is added to the culture vessel as depicted in step 22 in FIG. 6, and subsequently transferred to the image-grabber unit 15 by the operation robot 11. Concurrently with or after the transferring, vibration by the operation robot 11 allows the detachment solution to turn into the flowing state, and the solution distributes throughout the culture vessel (step 23). Thus, the operation robot 11 also serves as a vibration exciter in this embodiment.

As shown in FIG. 4, in the image-grabber unit 15, the operation robot 11 allows the culture liquid in the culture vessel 6 to turn into the flowing state as described above, and thereafter places the culture vessel 6 on the opening 5a of the table 5.

Next, in the image-grabber unit 15, an image at a certain position in the culture vessel is taken (step 24), and the image is transferred to the image processing apparatus 16 as a first image. Subsequently, after a lapse of a predetermined time and during keeping the flowing state of the culture liquid, an image is taken at the same position as the taking position of the first image (step 25), and the thus obtained image is transferred to the image processing apparatus 16 as a second image.

In the image processing apparatus 16, cell area ratio A and cell area ratio B, and common area ratio C are determined, and transferred to the overall control unit 17. The overall control unit 17 then calculates detachment rate $x_1$ as described above based on these area ratios (step 26). Next, the calculated detachment rate $x_1$ is compared with a predetermined threshold (step 27). When the detachment rate $x_1$ is less than the threshold, the process returns to the step 24, and the steps 24 to 27 are repeated again. Then, when the detachment rate $x_1$ is equal to or greater than the threshold, the culture vessel is again transferred from the image-grabber unit 15 to the operation unit 14, where a detachment stop solution is added to the culture vessel (step 28). Thereafter, further culture procedure is performed by conventional passage operations such as centrifugal separation, dispensing into multiple culture vessels, and transferring to the incubator 12. In the foregoing, when the detachment rate $x_1$ is less than the threshold in the step 27, the process returns to the step 24. However, when the flowing of the culture liquid come to a stop and the detached cell is static, the process returns to the step 23, and the step 23 to step 27 are repeated in which vibration of the culture vessel is carried out.

Figure 5:
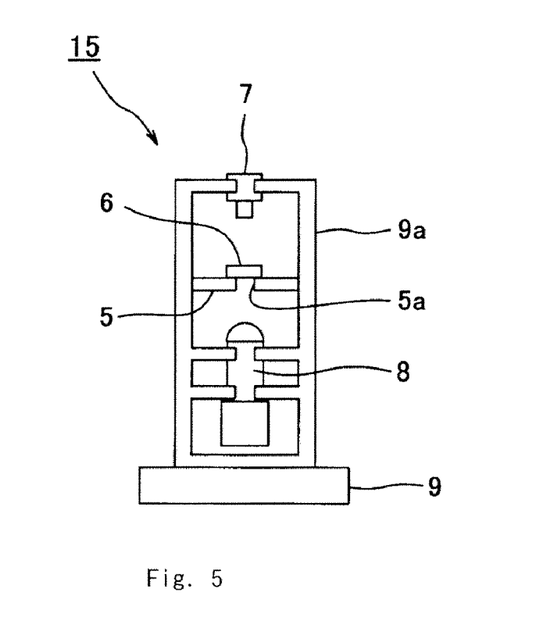
FIG. 5 shows a view schematically illustrating the construction of a image-grabber unit according to another embodiment of the present invention.

FIG. 5 shows a schematic construction of an image-grabber unit according to another embodiment. In the image-grabber unit 15 of this embodiment, vibrating by the operation robot 11 is not carried out, but vibration exciter 9 and vibration stage 9a are used to carry out the vibrating of the culture vessel. In this embodiment, the table 5, the lighting 7 and the microscope with camera 8 are fixed on the vibration stage 9a, and thus positional relationship of the culture vessel 6, the microscope with camera 8, and the lighting 7 disposed on the opening 5a of the table 5 would be fixed during vibration. According to such construction, shift of the taking positions of the images between at the time point of taking the first image and at the time point of taking the second image are obviated, therefore, it become possible to take the first image in the static state of the culture liquid in the culture vessel 6 followed by vibration and to take the second image, or alternatively, to take the first image and the second image while carrying out the vibration.

INDUSTRIAL APPLICABILITY

According to the method for evaluating cell detachment, the method of detaching cultured cells, the apparatus for evaluating cell detachment and the automated cell culture apparatus of the present invention, detachment of the cultured cells from the culture vessel can be automatically evaluated, thereby enabling applications in the field of regenerative medicine and the like.

The invention claimed is:

1. A method for evaluating cell detachment in which cell detachment from a culture vessel is evaluated, the method comprising the steps of:
taking a first image by imaging a certain position in a culture vessel;
taking a second image by imaging the certain position after taking the first image and also after allowing the culture liquid in the culture vessel to flow; and
evaluating, via an overall control apparatus, the cell detachment from the culture vessel by determining a cell area ratio A for a section where the cell is present in the first image, a cell area ratio B for a section where the cell is present in the second image, and a common area ratio C for a section where the cell is present in both the first image and the second image, and judging the cell detachment based on the cell area ratio A, the cell area ratio B and the common area ratio C.

2. The method for evaluating cell detachment according to claim 1, wherein when any cell attached to the culture vessel, and any floating cell detached from the culture vessel do not overlap one another,
the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell, by the following formula: $x_1=s_1/(f+s_1)=s_1/A$, based on a common adhesion cell area ratio $f=(C-AB)/(1+C-A-B)$ in the first image and the second image, and a floating cell total area ratio $s_1=A-f$ in the first image; and evaluating the cell detachment from the culture vessel based on the detachment rate $x_1$.

3. The method for evaluating cell detachment according to claim 1, wherein when any cell attached to the culture vessel, and any floating cell detached from the culture vessel do not overlap one another,
the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell detached from the culture vessel, by the following formula: $x_2=s_2/(f+s_2)=s_2/B$, based on a common adhesion cell area ratio $f=(C-AB)/(1+C-A-B)$ in the first image and the second image, and a floating cell total area ratio $s_2=B-f$ in the second image; and evaluating the cell detachment from the culture vessel based on the detachment rate $x_2$.

4. The method for evaluating cell detachment according to claim 1, wherein when a cell attached to the culture vessel may overlap with a floating cell detached from the culture vessel, but the floating cells do not overlap one another,
the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell detached from the culture vessel, by the following formula: $x_1=s_1/(f+s_1)$, based on a common adhesion cell area ratio $f=(C-AB)/(1+C-A-B)$ in the first image and the second image, and a floating cell total area ratio $s_1=(A-f)/(1-f)$ in the first image; and evaluating the cell detachment from the culture vessel based on the detachment rate $x_1$.

5. The method for evaluating cell detachment according to claim 1, wherein when a cell attached to the culture vessel may overlap with a floating cell detached from the culture vessel, but the floating cells do not overlap one another,
the step of evaluating cell detachment comprises: determining a detachment rate $x_2$ that is a proportion of a cell area ratio of the floating cell to sum total of a cell area ratio of the attached cell which is attached to the culture vessel and a cell area ratio of the floating cell detached from the culture vessel, by the following formula: $x_2=s_2/(f+s_2)$, based on a common adhesion cell area ratio $f=(C-AB)/(1+C-A-B)$ in the first image and the second image, and a floating cell total area ratio $s_2=(B-f)/(1-f)$ in the second image; and evaluating the cell detachment from the culture vessel based on the detachment rate $x_2$.

6. The method for evaluating cell detachment according to claim 1, wherein when a cell attached to the culture vessel may overlap with a floating cell detached from the culture vessel, and the floating cells may also overlap one another in duplicate at most,
the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell detached from the culture vessel, by the following formula: $x_1=s_1/(f+s_1)$, based on a common adhesion cell area ratio $f=(C-AB)/(1+C-A-B)$ in the first image and the second image, a projected area ratio of the floating cell $t_1=(A-f)/(1-f)$ in the first image, and a floating cell total area ratio $s_1=2-2(1-t_1)^{1/2}$ in the first image; and evaluating the cell detachment from the culture vessel based on the detachment rate $x_1$.

7. The method for evaluating cell detachment according to claim 1, wherein when a cell attached to the culture vessel may overlap with a floating cell detached from the culture vessel, and the floating cells may also overlap one another in duplicate at most, the step of evaluating cell detachment comprises: determining a detachment rate $x_2$ that is a proportion of a cell area ratio of the floating cell to sum total of a cell area ratio of the attached cell which is attached to the culture vessel and a cell area ratio of the floating cell detached from the culture vessel, by the following formula: $x_2=s_2/(f+s_2)$, based on a common adhesion cell area ratio $f=(C-AB)/(1+C-A-B)$ in the first image and the second image, a projected area ratio of the floating cell $t_2=(B-f)/(1-f)$ in the second image, and a floating cell total area ratio $s_2=2-2(1-t_2)^{1/2}$ in the second image; and evaluating the cell detachment from the culture vessel based on the detachment rate $x_2$.

8. The method for evaluating cell detachment according to claim 1, wherein when a cell attached to the culture vessel may overlap with a floating cell detached from the culture vessel, and the floating cells may overlap multiply one another irrespective of the presence or absence of the cell attached to the culture vessel, the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell detached from the culture vessel, by the following formula: $x_1=s_1/(f+s_1)$, based on a common adhesion cell area ratio $f=(C-AB)/(1+C-A-B)$ in the first image and the second image, a projected area ratio of the floating cell $t_1=(A-f)/(1-f)$ in the first image, and a floating cell total area ratio $s_1=-\ln(1-t_1)$ in the first image; and evaluating the cell detachment from the culture vessel based on the detachment rate $x_1$.

9. The method for evaluating cell detachment according to claim 1, wherein when a cell attached to the culture vessel may overlap with a floating cell detached from the culture vessel, and the floating cells may overlap multiply one another irrespective of the presence or absence of the cell attached to the culture vessel, the step of evaluating cell detachment comprises: determining a detachment rate $x_1$ that is a proportion of a cell area ratio of the floating cell to sum total of a cell area ratio of the attached cell which is attached to the culture vessel and a cell area ratio of the floating cell detached from the culture vessel, by the following formula: $x_2=s_2/(f+s_2)$, based on a common adhesion cell area ratio $f=(C-AB)/(1+C-A-B)$ in the first image and the second image, a projected area ratio of the floating cell $t_2=(B-f)/(1-f)$ in the second image, and a floating cell total area ratio $s_2=-\ln(1-t_2)$ in the second image; and evaluating the cell detachment from the culture vessel based on the detachment rate $x_2$.

10. A method of detaching culture cells, comprising the steps of:

placing a detachment solution into a culture vessel for allowing the cultured cell to be detached from the culture vessel;

taking a first image by imaging a certain position in a culture vessel;

taking a second image by imaging the certain position after taking the first image and also after allowing the culture liquid in the culture vessel to flow;

evaluating, via an overall control apparatus, the cell detachment from the culture vessel by determining a cell area ratio A for a section where the cell is present in the first image, a cell area ratio B for a section where the cell is present in the second image, and a common area ratio C for a section where the cell is present in both the first image and the second image, and judging the cell detachment based on the cell area ratio A, the cell area ratio B and the common area ratio C; and placing a detachment stop solution into the culture vessel.

11. The method of detaching cultured cells according to claim 10, wherein, in the step of evaluating the cell detachment, the evaluation of the cell detachment is repeated when the cell detachment from the culture vessel is insufficient.

12. An apparatus for evaluating cell detachment comprising:

a vibration exciter which allows the culture liquid in the culture vessel to turn into its flowing state;

a device for taking an image for obtaining a first image by imaging a certain position in a culture vessel and a second image by imaging the certain position after taking the first image and also after allowing the culture liquid in the culture vessel to flow; and a cell detachment evaluation means for evaluating the cell detachment from the culture vessel by determining a cell area ratio A for a section where the cell is present in the first image, a cell area ratio B for a section where the cell is present in the second image, and a common area ratio C for a section where the cell is present in both the first image and the second image, and judging the cell detachment based on the cell area ratio A, the cell area ratio B and the common area ratio C.

13. An automated cell culture apparatus comprising the apparatus for evaluating cell detachment according to claim 12, and an operation robot for carrying the culture vessel.

14. The automated cell culture apparatus according to claim 13 wherein the operation robot also serves as a vibration exciter in the apparatus for evaluating cell detachment.

* * * * *